US009052268B2

(12) United States Patent
Miyachi

(10) Patent No.: US 9,052,268 B2
(45) Date of Patent: Jun. 9, 2015

(54) ULTRASOUND DIAGNOSTIC APPARATUS AND METHOD OF PRODUCING ULTRASOUND IMAGE

(75) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 683 days.

(21) Appl. No.: 13/397,811

(22) Filed: Feb. 16, 2012

(65) Prior Publication Data

US 2012/0245468 A1  Sep. 27, 2012

(30) Foreign Application Priority Data

Mar. 22, 2011  (JP) .................. 2011-062098
Mar. 22, 2011  (JP) .................. 2011-062179

(51) Int. Cl.
G01N 29/07 (2006.01)
G01S 7/52 (2006.01)
G10K 11/34 (2006.01)
G01N 29/06 (2006.01)
A61B 8/08 (2006.01)
A61B 8/00 (2006.01)

(52) U.S. Cl.
CPC .......... G01N 29/07 (2013.01); G01N 2291/106 (2013.01); G01N 29/0672 (2013.01); A61B 8/5269 (2013.01); A61B 8/52 (2013.01); G01N 2291/02475 (2013.01); A61B 8/00 (2013.01); A61B 8/5207 (2013.01); G01S 7/52036 (2013.01); G01S 7/52049 (2013.01); G01S 7/52085 (2013.01); G10K 11/346 (2013.01)

(58) Field of Classification Search
CPC .......... A61B 8/00; A61B 8/52; A61B 8/5207; A61B 8/5269; G01S 7/52049; G01S 7/52085; G01S 7/52036; G01N 29/0672; G01N 29/07; G01N 2291/02475; G01N 2291/106
See application file for complete search history.

(56) References Cited

U.S. PATENT DOCUMENTS

2010/0076312 A1* 3/2010 Katsuyama .................. 600/443
2012/0183190 A1* 7/2012 Fukutani et al. ............. 382/128

FOREIGN PATENT DOCUMENTS

JP        05095946 A       4/1993
JP        8-317926 A       12/1996
JP        2007159652 A  *  6/2007
JP        2010-99452 A    5/2010

(Continued)

OTHER PUBLICATIONS

Cobbold, "Foundations of Biomedical Ultrasound." Aug. 14, 2006. Oxford University Press. p. 63.*

(Continued)

Primary Examiner — Tse Chen
Assistant Examiner — Nate S Sunwoo
(74) Attorney, Agent, or Firm — Sughrue Mion, PLLC

(57) ABSTRACT

An ultrasound diagnostic apparatus includes a region of interest setter which sets a region of interest on a B-mode image, a controller which performs transmission and reception of ultrasonic beams with forming transmission focuses at a plurality of points set on sound rays at a shallower position and a deeper position than the region of interest to acquire reception data for sound speed measurement, and a sound speed calculator which calculates an average local sound speed value in the region of interest on the basis of reception data for sound speed measurement.

20 Claims, 8 Drawing Sheets

(56) References Cited

FOREIGN PATENT DOCUMENTS

| JP | 2010207490 A | 9/2010 |
|----|--------------|--------|
| JP | 2010234013 A | 10/2010 |
| JP | 2011019751 A | 2/2011 |

OTHER PUBLICATIONS

Notification of Reasons for Refusal, dated Apr. 2, 2013, issued in corresponding JP Application No. 2011-062179, 3 pages in English and Japanese.

* cited by examiner

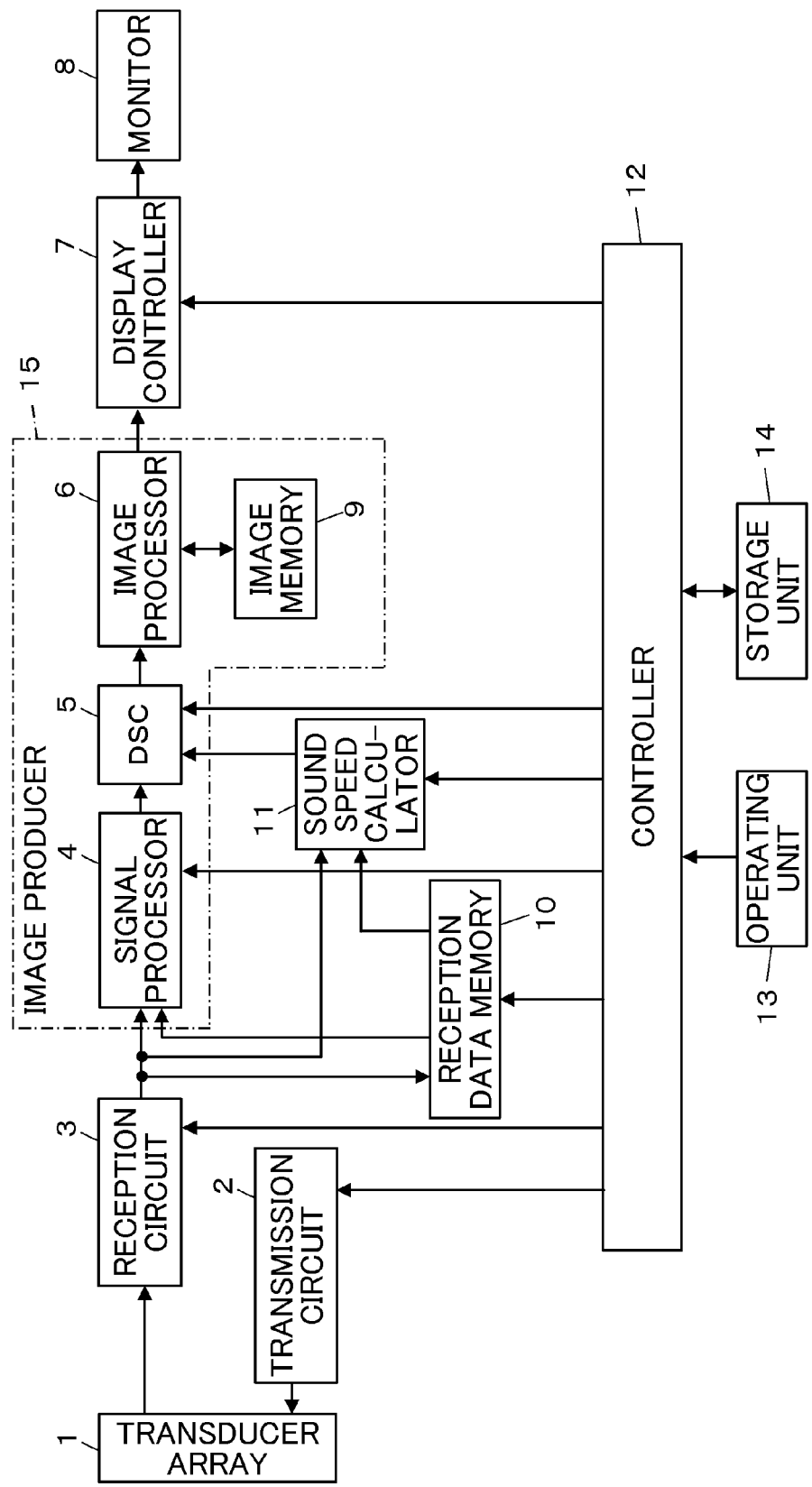

ULTRASOUND DIAGNOSTIC APPARATUS AND METHOD OF PRODUCING ULTRASOUND IMAGE

BACKGROUND OF THE INVENTION

The present invention relates to an ultrasound diagnostic apparatus and a method of producing an ultrasound image, and in particular, to an ultrasound diagnostic apparatus which performs transmission and reception of ultrasonic waves with respect to a transducer array of an ultrasound probe to perform both B-mode image production and sound speed measurement.

An ultrasound diagnostic apparatus using an ultrasound image has hitherto been put into practical use in the field of medicine. In general, this type of ultrasound diagnostic apparatus has an ultrasound probe embedded with a transducer array and an apparatus body connected to the ultrasound probe. An ultrasonic beam is transmitted from the ultrasound probe toward a subject, an ultrasonic echo from the subject is received by the ultrasound probe, and the reception signal is electrically processed by the apparatus body to produce an ultrasound image.

In recent years, in order to diagnose a site under diagnosis in the subject with satisfactory precision, sound speed in the site under diagnosis is measured.

For example, JP 2010-99452 A describes an ultrasound diagnostic apparatus which sets a plurality of lattice points in the vicinity of the site under diagnosis and calculates a local sound speed value on the basis of reception data obtained by transmitting and receiving an ultrasonic beam for each lattice point.

SUMMARY OF THE INVENTION

In the apparatus of JP 2010-99452 A, an ultrasonic beam is transmitted from the ultrasound probe toward the subject and received by the ultrasound probe, thereby obtaining the local sound speed value in the site under diagnosis. For example, it becomes possible to display a B-mode image and information of the local sound speed value in an overlapping manner.

However, when a region of interest is set, and a plurality of local sound speed values in a predetermined region are obtained, a lot of time may be spent depending on the positions of the set lattice points, or the like. An average local sound speed value in the region of interest may not be accurately calculated.

If there is a lesion portion in the site under diagnosis, the intensity of an ultrasonic echo from the lesion portion is lowered, and a low luminance region which is displayed black on the B-mode image is formed. With regard to the low luminance region, although there are many cases where it is effective for diagnosis to measure a local sound speed value as well as a B-mode image, since the intensity of the ultrasonic echo is low in the low luminance region, the reception signal may be likely to be influenced by noise, making it difficult to measure accurate sound speed.

The invention has been finalized in order to solve the problems inherent in the related art, and an object of the invention is to provide an ultrasound diagnostic apparatus and a method of producing an ultrasound image capable of an average local sound speed value in a region of interest in a short time with satisfactory precision.

An object of the invention is to provide an ultrasound diagnostic apparatus and a method of producing an ultrasound image capable of accurately measuring a local sound speed value of a low luminance region specified on a B-mode image.

An ultrasound diagnostic apparatus according to a first aspect of the invention comprises:
a transducer array;
a transmission circuit which transmits an ultrasonic beam from, the transducer array toward a subject;
a reception circuit which processes reception signals output from the transducer array having received an ultrasonic echo from the subject to produce reception data;
an image producer which produces a B-mode image on the basis of reception data obtained by the reception circuit;
a region of interest setter which sets a region of interest on the B-mode image produced by the image producer;
a controller which controls the transmission circuit and the reception circuit so as to perform transmission and reception of ultrasonic beams with forming transmission focuses at a plurality of points set on sound rays at a shallower position and a deeper position than the region of interest set by the region of interest setter to acquire reception data for sound speed measurement; and
a sound speed calculator which calculates an average local sound speed value in the region of interest on the basis of reception data for sound speed measurement,
wherein the points set at the shallower position are set in a shallow point region which is determined depending on a depth position of the region of interest, a length in a depth direction of the region of interest, and a width of simultaneously available transducers for transmission of each ultrasonic beam in the transducer array.

An ultrasound diagnostic apparatus according to a second aspect of the invention comprises:
a transducer array;
a transmission circuit which transmits an ultrasonic beam from the transducer array toward a subject;
a reception circuit which processes reception signals output from the transducer array having received an ultrasonic echo from the subject to produce reception data;
an image producer which produces a B-mode image on the basis of reception data obtained by the reception circuit;
a region of interest setter which sets a region of interest on the B-mode image produced by the image producer;
a low luminance region detector which detects a low luminance region having luminance equal to or lower than a predetermined value in the region of interest set by the region of interest setter;
a controller which controls the transmission circuit and the reception circuit so as to perform transmission and reception of ultrasonic beams with forming transmission focuses at a plurality of points set at a shallower position and a deeper position than the low luminance region detected by the low luminance region detector to acquire reception data for sound speed measurement; and
a sound speed calculator which calculates local sound speed values of the low luminance region on the basis of reception data for sound speed measurement on the assumption that sound speed is uniform between the shallower position and the deeper position.

A method of producing an ultrasound image according to a third aspect of the invention comprises the steps of:
transmitting an ultrasonic beam from a transducer array toward a subject on the basis of driving signals supplied from a transmission circuit;
processing reception signals output from the transducer array having received an ultrasonic echo from the subject by a reception circuit to produce reception data;

producing a B-mode image on the basis of obtained reception data;

setting a region of interest on the produced B-mode image;

setting a plurality of points on sound rays at a shallower position and a deeper position than the set region of interest, the points set at the shallower position being set in a shallow point region which is determined depending on a depth position of the region of interest, a length in a depth direction of the region of interest, and a width of the simultaneously available transducers for transmission of each ultrasonic beam the transducer array;

performing transmission and reception of ultrasonic beams with forming transmission focuses at the set points to acquire reception data for sound speed measurement; and calculating an average local sound speed value of the region of interest on the basis of acquired reception data for sound speed measurement.

A method of producing an ultrasound image according to a fourth aspect of the invention comprises the steps of:

transmitting an ultrasonic beam from a transducer array toward a subject on the basis of driving signals supplied from a transmission circuit;

processing reception signals output from the transducer array having received an ultrasonic echo from the subject by a reception circuit to produce reception data;

producing a B-mode image on the basis of obtained reception data;

setting a region of interest on the produced B-mode image;

detecting a low luminance region having luminance equal to or lower than a predetermined value in the region of interest;

setting a plurality of points at a shallower position and a deeper position than the detected low luminance region;

performing transmission and reception of ultrasonic beams with forming transmission focuses at the set points to acquire reception data for sound speed measurement; and calculating local sound speed values of the low luminance region on the basis of acquired reception data for sound speed measurement on the assumption that sound speed is uniform between the shallower position and the deeper position.

BRIEF DESCRIPTION OF THE DRAWINGS

FIG. 1 is a block diagram showing the configuration of an ultrasound diagnostic apparatus according to Embodiment of the invention.

DETAILED DESCRIPTION OF THE INVENTION

Figure 2A:
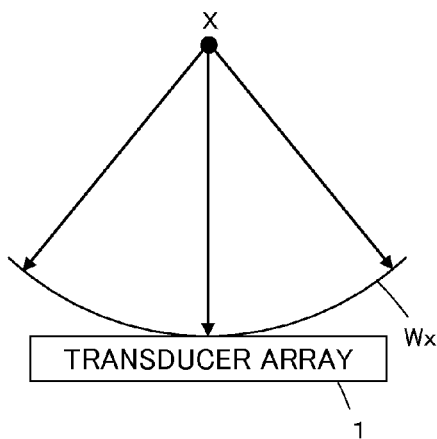
FIGS. 2A and 2B are diagrams schematically showing the principle of sound speed calculation in Embodiment 1.

Hereinafter, embodiments of the invention will be described with reference to the accompanying drawings.

Embodiment 1

FIG. 1 shows the configuration of an ultrasound diagnostic apparatus according to Embodiment 1 of the invention. The ultrasound diagnostic apparatus includes a transducer array 1, and a transmission circuit 2 and a reception circuit 3 are connected to the transducer array 1. A signal processor 4, a DSC (Digital Scan Converter) 5, an image processor 6, a display controller 7, and a monitor 8 are sequentially connected to the reception circuit 3. An image memory 9 is connected to the image processor 6. A reception data memory 10 and a sound speed calculator 11 are connected to the reception circuit 3.

A controller 12 is connected to the signal processor 4, the DSC 5, the display controller 7, the reception data memory 10, and the sound speed calculator 11. An operating unit 13 and a storage unit 14 are connected to the controller 12.

The transducer array 1 has a plurality of ultrasound transducers arranged in a one-dimensional or two-dimensional manner. These ultrasound transducers transmit ultrasonic waves in response to driving signals supplied from the transmission circuit 2, receive an ultrasonic echo from the subject, and output reception signals. Each ultrasound transducer is constituted by a vibrator in which electrodes are formed at both ends of a piezoelectric body made of piezoelectric ceramic represented by PZT (Pb (lead) zirconate titanate), a polymer piezoelectric device represented by PVDF (polyvinylidene difluoride), piezoelectric single crystal represented by PMN-PT (lead magnesium niobate-lead titanate solid solution), or the like.

If a pulsed or continuous-wave voltage is applied to the electrodes of the vibrator, the piezoelectric body expands and contracts. Pulsed or continuous-wave ultrasonic waves are produced from the vibrators and synthesized to form an ultrasonic beam. When receiving the propagating ultrasonic waves, the vibrators produce electric signals, and the electric signals are output as the reception signals of the ultrasonic waves.

The transmission circuit 2 includes, for example, a plurality of pulsars. The transmission circuit 2 adjusts the delay amount of each of the driving signals on the oasis of a transmission delay pattern selected in response to control signals from the controller 12 such that ultrasonic waves transmitted from a plurality of ultrasound transducers of the transducer array 1 form an ultrasonic beam, and supplies the driving signals to a plurality of ultrasound transducers.

The reception circuit 3 amplifies the reception signal transmitted from each ultrasound transducer of the transducer array 1 and performs A/D conversion to produce reception data.

The signal processor 4 performs a reception focus process by giving the delay to each piece of reception data in accordance with sound speed or the distribution of sound speed set on the basis of a reception delay pattern selected in response to a control signal from the controller 12 for reception data produced by the reception circuit 3 and adding reception data. The focus of the ultrasonic echo is narrowed to produce a sound ray signal. The signal processor 4 corrects attenuation depending on the distance in accordance with the depth of the reflection position of the ultrasonic wave, and performs an envelope detection process, thereby producing a B-mode image signal which is tomographic image information relating to the tissue of the subject.

The DSC 5 converts (raster-converts) the B-mode image signal produced by the signal processor 4 to an image signal based on a normal television signal scan system.

The image processor 6 performs various necessary image processes, such as a gradation process, on the B-mode image signal input from the DSC 5, and then outputs the B-mode image signal to the display controller 7 or stores the B-mode image signal in the image memory 9.

The signal processor 4, the DSC 5, the image processor 6, and the image memory 9 form an image producer 15.

The display controller 7 displays an ultrasound diagnostic image on the monitor 8 on the basis of the B-mode image signal subjected to the image process by the image processor 6.

The monitor 8 includes, for example, a display device, such as an LCD, and displays the ultrasound diagnostic image under the control of the display controller 7.

The reception data memory 10 stores reception data output from the reception circuit 3 in time series for each channel. The reception data memory 10 stores information (for example, parameters representing the depth of the reflection position of the ultrasonic wave, the density of the scan lines, and the width of the field of vision) relating to a frame rate input from the controller 12 in association with reception data.

The sound speed calculator 11 calculates a local sound speed value on the basis of reception data stored in the reception data memory 10 under the control of the controller 12.

The controller 12 controls the respective units of the ultrasound diagnostic apparatus on the basis of a command input from the operating unit 13 by the operator.

The operating unit 13 is used when the operator performs an input operation, and constitutes a region of interest setter of the invention. The operating unit 13 may be a keyboard, a mouse, a trackball, a touch panel, or the like.

The storage unit 14 stores an operation program or the like, and as a recording medium in the storage unit 30, a recording medium, such as a hard disk, a flexible disk, an MO, an MT, a RAM, a CD-ROM, a DVD-ROM, an SD card, a CF card, or a USB memory, a server, or the like may be used.

The signal processor 4, the DSC 5, the image processor 6 the display controller 7, and the sound speed calculator 11 are constituted by a CPU and an operation program which causes the CPU to perform various processes, and these may be constituted by digital circuits.

The operator can select one of the following three display modes from the operating unit 13. That is, display can be performed in a desired mode from among a mode in which a B-mode image is displayed alone, a mode in which an average local sound speed value in a region of interest is displayed on a B-mode image in an overlapping manner, and a mode in which a B-mode image and an average local sound speed value in a region of interest are displayed in parallel.

When displaying a B-mode image, first, ultrasonic waves are transmitted from a plurality of ultrasound transducers of the transducer array 1 in response to driving signals supplied from the transmission circuit 2. A reception signal from each ultrasound transducer having received an ultrasonic echo from the subject is output to the reception circuit 3, and reception data is produced by the reception circuit 3. A B-mode image signal is produced by the signal processor 4 to which reception data is input, and the B-mode image signal is raster-converted by the DSC 5. The B-mode image signal is subjected to various image processes by the image processor 6, and then an ultrasound diagnostic image is displayed on the monitor 8 on the basis of the B-mode image signal by the display controller V.

The calculation of a local sound speed value can be performed by, for example, the method described in JP 2010-99452 A filed in the name of this applicant.

Figure 2B:
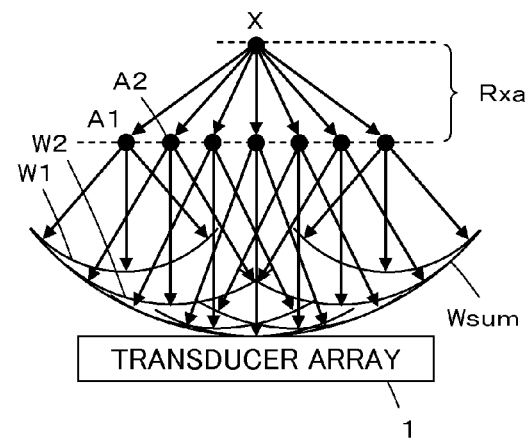

As shown in FIG. 2A, according to this method, when the ultrasonic waves are transmitted into the subject, a received wave Wx which reaches the transducer array 1 from a lattice point X as a reflection point of the subject is focused. Then, as shown in FIG. 2B, a plurality of lattice points A1, A2, . . . are arranged at regular intervals at positions shallower than the lattice point X, that is, at positions close to the transducer array 1. A synthesized wave Wsum of received waves W1, W2, . . . from a plurality of lattice points A1, A2, . . . having received the received wave from the lattice point X coincides with a received wave Wx from the lattice point X by the Huygens principle, and with the use of this point, the local sound speed value is obtained at the lattice point X.

First, the optimum sound speed values of all the lattice points X, A1, A2, . . . are obtained. The optimum sound speed value is a speed sound value such that imaging is performed with focus calculation based on the set speed sound for each lattice point to form an ultrasound image, and when the set sound speed changes in various ways, contrast of an image and sharpness become highest. For example, as described in JP 8-317926 A, the optimum sound speed value can be determined on the basis of contrast of an image, a spatial frequency in a scan direction, dispersion, or the like.

Next, the waveform of the virtual received wave Wx emitted from the lattice point X is calculated using the optimum sound speed value for the lattice point X.

A virtual local sound speed value V at the lattice point X changes in various ways to calculate the virtual synthesized wave Wsum of the received waves W1, W2, . . . from the lattice points A1, A2, . . . . . At this time, it is assumed that the sound speed is uniform in a region Rxa between the lattice point X and each of the lattice points A1, A2, . . . , and is equal to the local sound speed value V at the lattice point X. The time until the ultrasonic wave propagating from the lattice point X reaches the lattice points A1, A2, . . . becomes XA1/V, XA2/V, . . . . XA1, XA2, . . . are the distance between the respective lattice points A1, A2, . . . and the lattice point X. Accordingly, reflected waves emitted from the lattice points A1, A2, . . . with the delay of the time XA1/V, XA2/V, . . . are synthesized, thereby obtaining the virtual synthesized wave Wsum.

Next, errors between a plurality of virtual synthesized waves Wsum calculated by changing the virtual local sound speed value V at the lattice point and the virtual received wave Wx from the lattice point X are calculated, and the virtual local sound speed value V with the minimum error is determined as the local sound speed value at are at the lattice point X. As the method of calculating the error between the virtual synthesized wave Wsum and the virtual received wave Wx from the lattice point X, a method in which an intercorrelation is made, a method in which phase matching addition is performed while the delay obtained from the synthesized wave Wsum is applied to the received wave Wx, a method in which phase matching addition is performed while the delay obtained from the received Wx is applied to the synthesized wave Wsum, or the like may be used.

In the above-described manner, it is possible to calculate the local speed sound value in the subject on the basis of reception data produced by the reception circuit 3 with high precision. Similarly, it is possible to produce the sound speed map which represents the distribution of the local sound speed values in the set region of interest.

Figure 3:
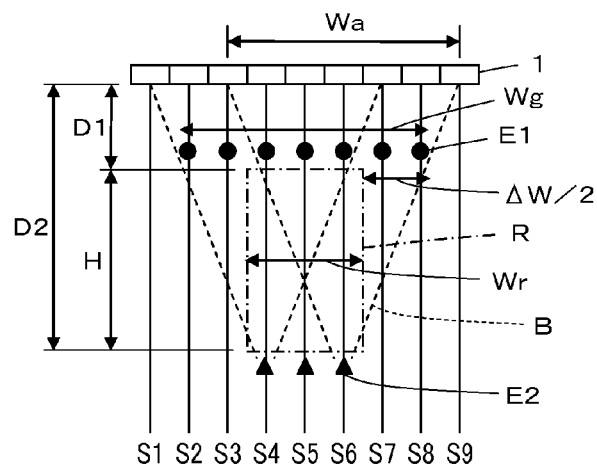
FIG. 3 is a diagram showing set lattice points in Embodiment 1.

A method of setting lattice points in Embodiment 1 will be described with reference to FIG. 3. In FIG. 3, for simplification, the transducer array 1 is shown in which nine ultrasound transducers are arranged, and sound rays S1 to S9 are formed at the array pitch of the ultrasound transducers. A region R of interest having a width Wr in the azimuth direction and vertical length H in the depth direction stretches over the sound rays S4 to S6. A shallowest portion has a depth 91 and a deepest portion has a depth 92.

With regard to the region R of interest, lattice points are set at a shallow position from the region R of interest, that is, at a position close to the transducer array 1 and at a deep position from the region R of interest, that is, on a sound ray opposite to the transducer array 1. In FIG. 3, a plurality of lattice points E1 indicated by "●" are set on the sound rays S2 to S8 at a shallow position from the region R of interest and adjacent positions in the azimuth direction, and a plurality of lattice points E2 indicated by "▲" are set on the sound rays S4 to S6 at a deep position from the region R of interest and adjacent positions in the azimuth direction. At this time, the lattice points E1 set at a shallow position from the region R of interest are set in a shallow lattice point region which is determined in accordance with a depth D1 of the shallowest portion of the region R of interest, a vertical length H in the depth direction of the region R of interest, and a width of simultaneously available transducers for transmission of each ultrasonic beam in the transducer array 1. On the assumption that the sound speed in the region between each of the lattice points E2 set at the deep position and a plurality of lattice points E1 set at the shallow position is uniform, the local sound speed values between the regions are calculated, and the average local sound speed value in the region R of interest is calculated.

Next, the operation of Embodiment 1 will be described.

First, an ultrasonic beam is transmitted from a plurality of ultrasound transducers of the transducer array 1 in response to the driving signal from the transmission circuit 2, and the reception signal from each ultrasound transducer having received an ultrasonic echo from the subject is output to the reception circuit 3 to produce reception data. The display controller 7 displays a B-mode image is displayed on the monitor 8 on the basis of a B-mode image signal produced by the image producer 15.

If the B-mode image is displayed on the monitor 8, the operator operates the operating unit 13 to set the region R of interest on the B-mode image, and as shown in FIG. 3, the controller 12 sets the lattice points E2 on all the sound rays S4 to S6 passing through the region R of interest at the deep position from the region R of interest. Subsequently, the controller 12 sets a shallow lattice point region having a width Wg in the azimuth direction at a shallow position from the region R of interest, and the lattice points E1 are set on all the sound rays S2 to S8 passing through the shallow lattice point region.

The shallow lattice point region is set to fall within the region of either ultrasonic beam which is transmitted and received when a transmission focus is formed at each of the lattice points E2 set at the deep position, such that the lattice points E1 can be set only at a position necessary for obtaining a synthesized of received waves with little distortion when transmitting and receiving the ultrasonic beam B. This is because a synthesized wave of received waves from a plurality of lattice points E1 at the shallow position having received a received wave from the lattice point E2 at the deep position coincides with the received wave from the lattice point E2 by the Huygens principle, and with the use of this point, the local sound speed values are calculated. If the shallow lattice point region is set in the above-described manner, when $\Delta W = Wg - Wr$, $\Delta W : H = Wa : (H + D1)$ is established, and the relational expression $Wg = Wr + Wa/(1 + (D1/H))$ is obtained. That is, the width Wg of the shallow lattice point region is determined in an optimum range according to the depth position D1 of the region R of interest, the length H in the depth direction of the region R of interest, and the width Wa of simultaneously available transducers for transmission of each ultrasonic beam in the transducer array 1.

In this way, the controller 12 performs control such that the transmission circuit 2 and the reception circuit 3 form a transmission focus at each of the lattice points E1 and E2 set with the region R of interest interposed therebetween in the depth direction, sequentially perform transmission and reception of the ultrasonic beam B for sound speed measurement, and acquire received waves from the lattice points E1 and E2.

Reception data for sound speed measurement produced by the reception circuit 3 each time the ultrasonic beam B is received is sequentially stored in the reception data memory 10. If reception data for sound speed measurement acquired through transmission and reception of the ultrasonic beam B when a transmission focus is formed at all the lattice points E1 and E2 is stored in the reception data memory 10, the sound speed calculator 11 assumes that the sound speed in each region between each of the lattice points E2 set at the deep position and a plurality of lattice points E1 set at the shallow position, calculates the local sound speed values of the respective regions using reception data for sound speed measurement stored in the reception data memory 10, and averages the local sound speed values to calculate and store the average local sound speed value in the region R of interest.

At this time, as described with reference to FIG. 2B, a synthesized wave of received waves from a plurality of lattice points E1 at the shallow position having received a received wave from one lattice point from among the lattice points E2 at the deep position coincides with a received wave received from one lattice point E2 by the Huygens principle. With the use of this point, the local sound speed values of the region between the lattice points E1 and E2 are calculated.

The sound speed calculator 11 defines the average of the thus-calculated local sound speed values of the region between each of the lattice points E2 and the lattice point E1 as the average local sound speed value of the region R of interest.

The setting of the length Wg of the shallow lattice point region is performed as follows, for example.

Figure 4A:
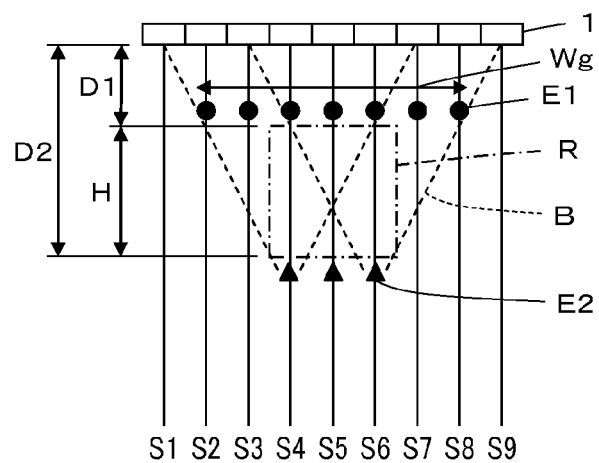
FIG. 4A is a diagram showing the positions of lattice points set for a region of interest at a shallow position.
Figure 4B:
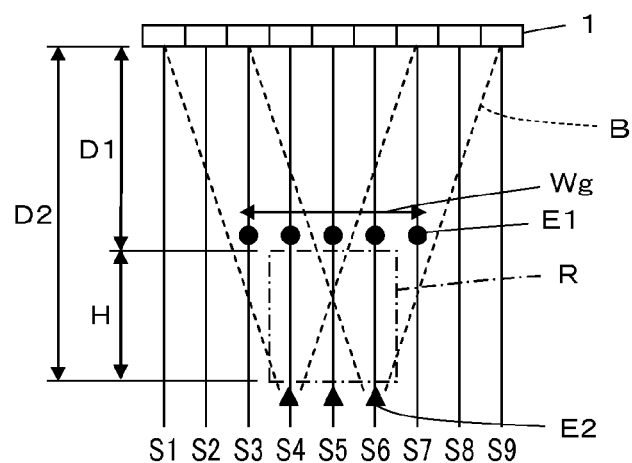
FIG. 4B is a diagram showing the positions of lattice points set for a region of interest at a deep position.

When the values of the length H in the depth direction of the region R of interest and the width Wa of simultaneously available transducers for transmission of each ultrasonic beam B are fixed, and the value of the depth position D1 of the region R of interest is changed, and when the region A of interest is at the depth position D1 shown in FIG. 4A, the shallow lattice point region is set to include the sound rays S2 to S8. Meanwhile, as the depth position D1 of the region R of interest is deepened, the region width of the ultrasonic beam B which is transmitted and received when a transmission focus is formed at the lattice point E2 is shortened, and the shallow lattice point region is set to be short. When the region A of interest is at the depth position D1 shown in FIG. 4B, the shallow lattice point region is set to include the sound rays S3 to S7.

Figure 5A:
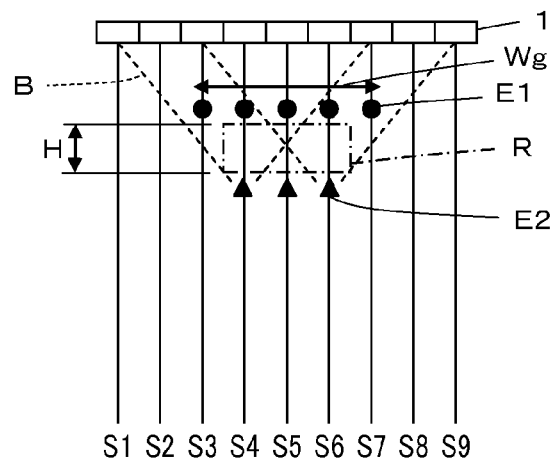
FIG. 5A is a diagram showing the positions of lattice points set for a short region of interest in a depth direction.
Figure 5B:
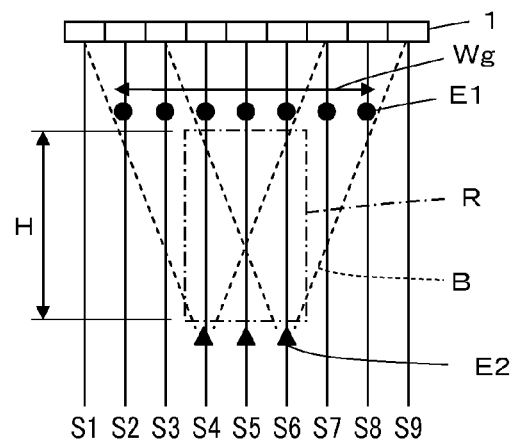
FIG. 5B is a diagram showing the positions of lattice points set for a long region of interest in a depth direction.

When the values of the depth position D1 of the region R of interest and the width Wa of simultaneously available transducers for transmission of each ultrasonic beam B are fixed, and the value of the length H in the depth direction of the region R of interest is changed, and when the region R of interest has the length H shown in FIG. 5A, the shallow lattice point region is set to include the sound rays S3 to S7. Meanwhile, as the length H in the depth direction of the region R of interest is extended, the region width of the ultrasonic beam B which is transmitted and received when a transmission focus is formed at the lattice point E2 is extended, and the shallow lattice point region is set to be long. When the region R of interest has the length H shown in FIG. 5B, the shallow lattice point region is set to include the sound rays S2 to S8.

Figure 6A:
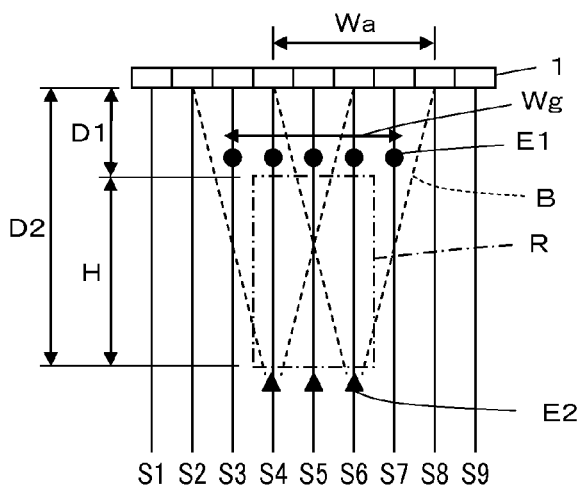
FIG. 6A is a diagram showing the positions of lattice points set when an ultrasonic beam with a short width of simultaneously available transducers for transmission is transmitted and received.
Figure 6B:
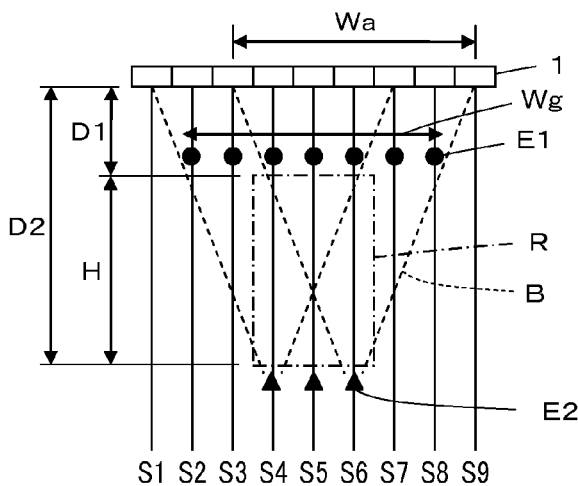
FIG. 6B is a diagram showing the positions of lattice points set when an ultrasonic beam with long width of simultaneously available transducers for transmission is transmitted and received.

When the values of the depth position D1 of the region R of interest and the length H in the depth direction of the region R of interest are fixed, and the value of the width Wa of simultaneously available transducers for transmission of each ultrasonic beam B is changed, and when the ultrasonic beam B is transmitted and received with the width Wa having the size shown in FIG. 6A, the shallow lattice point region is set to include the sound rays S3 to S7. Meanwhile, as the width Wa increases, the region width of the ultrasonic beam B which is transmitted and received when a transmission focus is formed at the lattice point E2 is extended, and the shallow lattice point region is set to be long. When the width Wa increases as shown in FIG. 6B, the shallow lattice point region is set to include the sound rays S2 to S8.

In this way, with the setting of the region R of interest, the lattice point E1 which is set at a shallow position from the region R of interest and the lattice point E2 which is set at a deep position from the region R of interest are set at the optimum, positions. Therefore, becomes possible to calculate the local sound speed values and the average local sound speed value in the region R of interest a short time with satisfactory precision.

Embodiment 2

In Embodiment 1, a configuration may be made in which the average local sound speed value in the region R of interest is measured, and the sound speed map in the region R of interest is produced.

Figure 7:
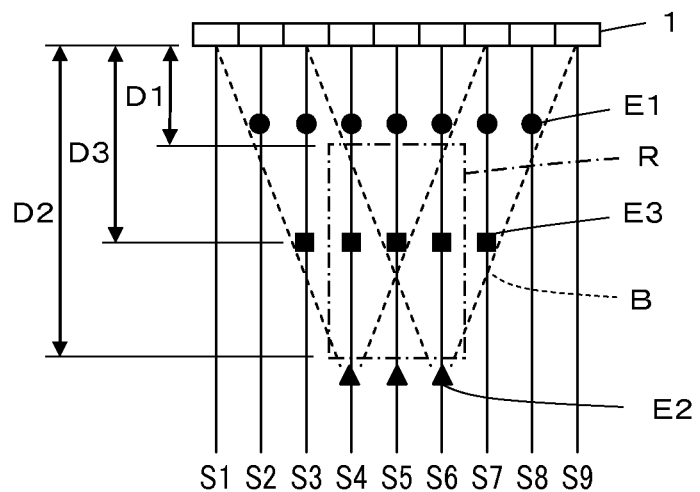
FIG. 7 is a diagram showing set lattice points in Embodiment 2.

For example, as shown in FIG. 7, if a region R of interest is set on a B-mode image by an operation from the operating unit 13, the controller 12 sets lattice point E1 and E2 at a shallow position and a deep position from the region R of interest, and sets a plurality of lattice points E3 for a sound speed map indicated by "■" in the azimuth direction at a position D3 between the lattice points E1 and E2. It is preferable that the lattice point E3 for a sound speed map is set to fall within the region of either ultrasonic beam B transmitted and received when a transmission focus is formed at each lattice point E2 set at a shallow position.

Subsequently, the controller 12 performs control such that the transmission circuit 2 and the reception circuit 3 form a transmission focus at each of the lattice points E1 and E2 and the lattice points E3 for a sound speed map, and sequentially perform transmission and reception of an ultrasonic beam for sound speed measurement, and reception data for sound speed measurement produced by the reception circuit 3 is sequentially stored in the reception data memory 10. As in Embodiment 1, the sound speed calculator 11 calculates the local sound speed values and the average local sound speed value in the region R of interest using reception data relating to the lattice points E1 and E2 stored in the reception data memory 10. Meanwhile, the sound speed calculator 11 calculates the local sound speed values of the lattice points E1, E2, and E3 using reception data relating to the lattice points E1 and E2 and reception data for a sound speed map relating to the lattice points E3 for a sound speed map, and produces the sound speed map in the region R of interest.

Data relating to the sound speed map produced by the sound speed calculator 11 is raster-converted by the DSC 5, subjected to various processes in the image processor 6, and sent to the display controller 7. The B-mode image and the sound speed map are displayed on the monitor 8 in an overlapping manner (for example, display where color or luminance changes depending on the local sound speed value or display where points having the same local sound speed value are connected by a line), or the B-mode image and the sound speed map image are displayed in parallel on the monitor 8 in accordance with the display mode from the operating unit 13 by the operator.

In this way, it becomes possible to measure the local sound speed values or the average local sound speed value in the region R of interest and to perform both production of the B-mode image and production of the sound speed map.

Embodiment 3

In Embodiments 1 and 2, the sequence may be set such that, as the lattice points are at a short distance, the ultrasonic beam B which is transmitted and received when a transmission focus is formed at each lattice point set by the controller 12 is transmitted and received at a short time interval.

Figure 8:
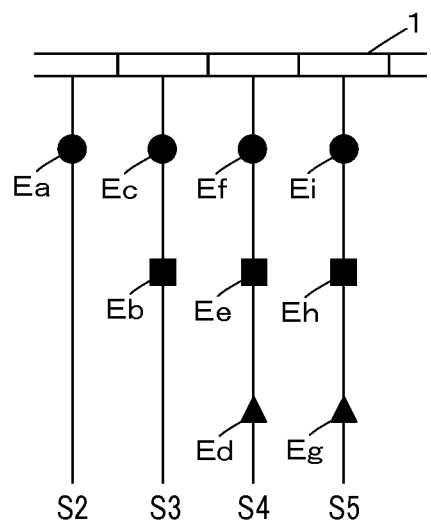
FIG. 8 is a diagram showing a sequence in which a transmission focus of an ultrasonic beam is formed at each lattice point in Embodiment 3.

For example, with regard to lattice points shown in FIG. 8, a transmission focus of an ultrasonic beam can be formed in order of lattice points Ea, Ec, Ef, Ei, ..., Eb, Ee, ..., that is, a transmission focus of an ultrasonic beam can be sequentially formed at the lattice points at the same depth in the azimuth direction, and this can be repeated in the depth direction. A transmission focus of an ultrasonic beam may be formed in order of the lattice points Ea, Eb, Ec, Ed, Ee, ..., that is, a transmission focus of an ultrasonic beam may be formed at the lattice points set on the same sound ray, and this may be repeated for each sound ray.

In this way, transmission and reception of an ultrasonic beam are performed when a transmission focus formed sequentially from a lattice point at a snort distance, thereby obtaining a reception signal of a lattice point at a short distance at a short time interval and more accurately measuring the average local sound speed value in the region R of interest.

Although in Embodiments 1 to 3, reception data output from the reception circuit 3 is temporarily stored in the reception data memory 10, and the sound speed calculator 11 calculates the average local sound speed value of the region R of interest using reception data stored in the reception data memory 10, the sound speed calculator 11 may directly receive reception data output from the reception circuit 3 as input to calculate the average local sound speed value in the region R of interest.

In Embodiments 1 to 3, for simplification, the number of openings of the transducer array 1 shown in the drawing, that is, the number of sound rays, the number of lattice points, and the like are small, the invention is not limited thereto. It is preferable to set the number of openings and the number of lattice points appropriate for diagnosis based on the B-mode image and sound speed measurement.

Embodiment 4

Figure 9:
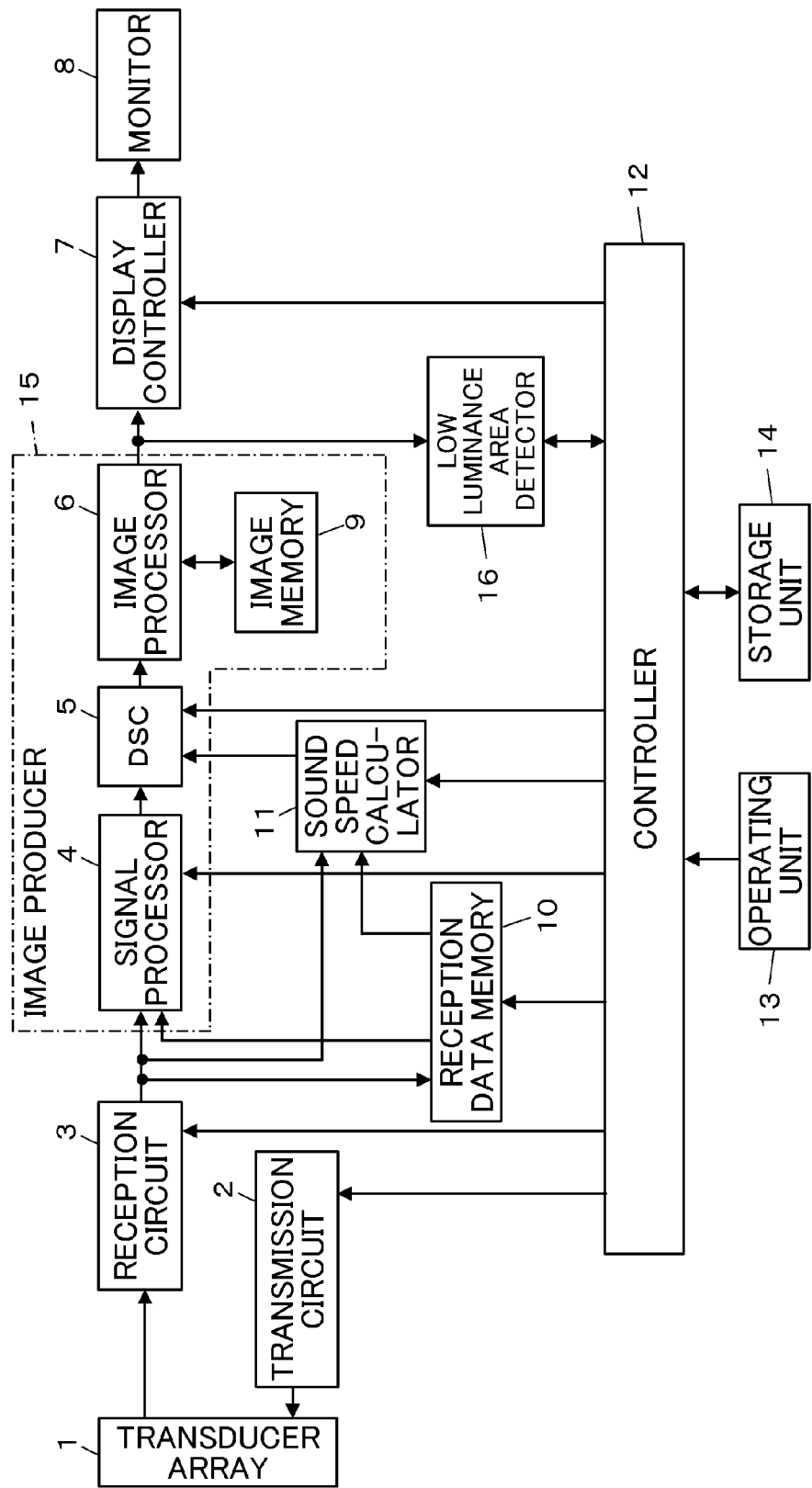
FIG. 9 is a block diagram showing the configuration of an ultrasound diagnostic apparatus according to Embodiment 4.

FIG. 9 shows the configuration of an ultrasound diagnostic apparatus according to Embodiment 4. This ultrasound diagnostic apparatus is provided to accurately measure the local sound speed values of a low luminance region specified on the B-mode image. A low luminance region detector 16 is connected to the image processor 6 and the controller 12 of the ultrasound diagnostic apparatus of Embodiment 1 shown in FIG. 1.

The low luminance region detector 16 detects a low luminance region having luminance equal to or lower than a predetermined value on the B-mode image on the basis of the B-mode image signal subjected to the image process in the image processor 6.

The sound speed calculator 11 calculates the local sound speed values of the low luminance region detected by the low luminance region detector 16 on the basis of reception data stored in the reception data memory 10 under the control of the controller 12.

The calculation of the local sound speed values can be performed as in Embodiment 1 by the method described in JP 2010-99452 A with a region Rxa between a lattice point X and each of lattice points A1, A2, . . . in FIG. 2B as a low luminance region having luminance equal to or lower than a predetermined value. That is, when calculating a virtual synthesized wave Wsum of received waves W1, W2, . . . from the lattice points A1, A2, . . . , in the region Rxa, reflection intensity is small, that is, a change in acoustic impedance $Z=\rho \cdot c$ ($\rho$ is density, and c is sound speed) is small, and the sound speed c can be substantially regarded to be uniform. This is because the density $\rho$ in the subject does not significantly change, and with a change in the density $\rho$ caused by a change in the sound speed c, there is little possibility that the value $Z=\rho \cdot c$ does not change. For this reason, it can be assumed that the sound speed c in the region Rxa is uniform and equal to the local sound speed value V at the lattice point X.

Figure 10:
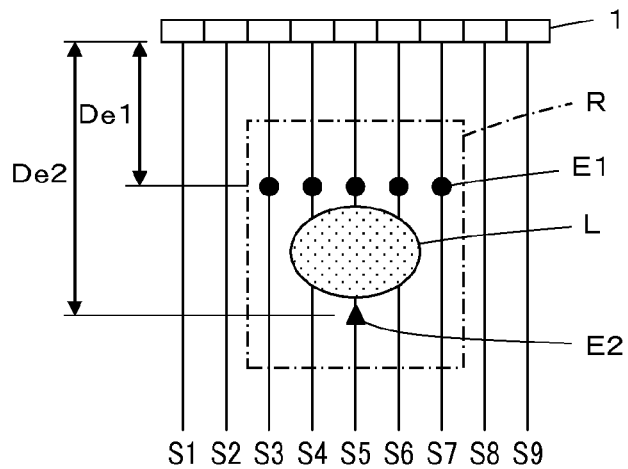
FIG. 10 is a diagram showing set lattice points in Embodiment 4.

A method of setting lattice points in Embodiment 4 will be described with reference to FIG. 10. In FIG. 10, for simplification, the transducer array 1 is shown in which nine ultrasound transducers are arranged, and sound rays S1 to S9 are formed at the array pitch of the ultrasound transducers. There is a low luminance region L to stretch over the sound rays S4 to S6.

With regard to the low luminance region L, lattice points are set at a shallow position from the low luminance region L, that is, at a position close to the transducer array 1 and at a deep position from the low luminance region L, that is, a sound ray opposite to the transducer array 1. In FIG. 10, a plurality of lattice points E1 indicated by "●" are set on sound rays S3 to S7 at a position corresponding to a depth De1 shallower than the low luminance region L, and one lattice point E2 indicated by "▲" is set on a sound ray S5 at a position corresponding to a depth De2 deeper than the low luminance region L. The local sound speed values of the low luminance region L are calculated on the assumption that sound speed in a region between the shallow position corresponding to the depth De1 and the deep position corresponding to the depth De2 is uniform.

Next, the operation of Embodiment 4 will be described.

First, an ultrasonic beam is transmitted from a plurality of ultrasound transducers of the transducer array 1 in response to the driving signal from the transmission circuit 2, and the reception signal from each ultrasound transducer having received an ultrasonic echo from the subject is output to the reception circuit 3 to produce reception data. The display controller 7 displays a B-mode image is displayed on the monitor 8 on the basis of a B-mode image signal produced by the image producer 15.

If the operator operates the operating unit 13 and a region R of interest is set on a B-mode image displayed on the monitor 8, the low luminance region detector 16 detects a low luminance region L having luminance equal to or lower than a predetermined value in the region R of interest on the basis of the B-mode image signal produced by the image producer 15. If the low luminance region L is detected in the region R of interest, as shown in FIG. 10, the controller 12 sets a plurality of lattice points E1 at a position corresponding to a depth De1 shallower than the low luminance region L and sets one lattice point E2 at a position corresponding to a depth De2 deeper than the low luminance region L. That is, the lattice points E1 and the lattice point E2 are set such that the low luminance region L is interposed in the depth direction.

Next, the controller 12 performs control such that the transmission circuit 2 and the reception circuit 3 form a transmission focus at each of the lattice points E1 and E2 set in the above-described manner, sequentially perform transmission and reception of an ultrasonic beam for sound speed measurement, and capture received waves from the lattice points E1 and E2.

Reception data for sound speed measurement produced by the reception circuit 3 each time an ultrasonic beam is received is sequentially stored in the reception data memory 10. If reception data for sound speed measurement acquired through transmission and reception of an ultrasonic beam when a transmission focus is formed at all the lattice points E1 and E2 is stored in the reception data memory 10, the sound speed calculator 11 assumes that sound speed in the region between the lattice point E1 having a depth De1 and the lattice point E2 having a depth De2 is uniform, and calculates the local sound speed value of a region between the depth De1 and the depth De2 using reception data for sound speed measurement stored in the reception data memory 10.

At this time, as described with reference to FIG. 2B, a synthesized wave of received waves from a plurality of lattice points E1 at the shallow position corresponding to the depth De1 having received a received wave from the lattice point E2 at the deep position corresponding to the depth De2 coincides with a received wave from the lattice point E2 by the Huygens principle, and with the use of this point, the local sound speed values of the region between the depth De1 and the depth De2 are calculated.

The sound speed calculator 11 defines the thus-calculated local sound speed values of the region between the depth De1 and the depth De2 as the local sound speed values of the low luminance region L.

As described above, reception data for sound speed measurement acquired through transmission and reception of the ultrasonic beam when a transmission focus is formed at the lattice points set at the shallow position from the low luminance region 2 and at the deep position from the low luminance region 2, excluding the low luminance region L with low ultrasonic echo intensity is used, thereby accurately measuring the local sound speed values of the loin luminance region L.

As described above, a synthesized wave of received waves from a plurality of lattice points E1 at the shallow position having received from a received wave from the lattice point E2 at the deep position coincides with a received wave from the lattice point E2, and with the use of this point, the local sound speed values of the low luminance region L are obtained. Therefore, it is preferable to set a larger number of lattice points E1 at the shallow position than the lattice points E2 set at the deep position.

Figure 11:
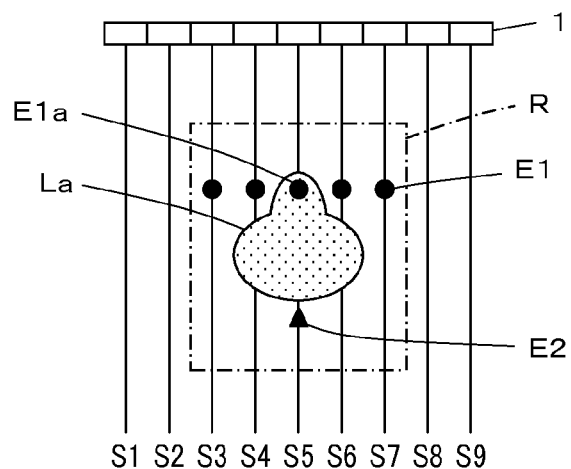
FIG. 11 is a diagram showing set lattice points in a modification of Embodiment 4.

Although in FIG. 10, all of a plurality of lattice points E1 at the depth De1 are the shallow position from the low luminance region L, as shown in FIG. 11, some lattice points E1a from among a plurality of lattice points E1 may be located in the low luminance region La depending on the shape of the low luminance region La. Meanwhile, since the intensity of an ultrasonic echo from the lattice point E1a in the low luminance region La is low, reception data for sound speed measurement acquired through transmission and reception of an ultrasonic beam when a transmission focus is formed at the lattice point E1a has a low degree of contribution to the calculation of the local sound speed values of the region between the depth De1 and the depth De2.

Figure 12:
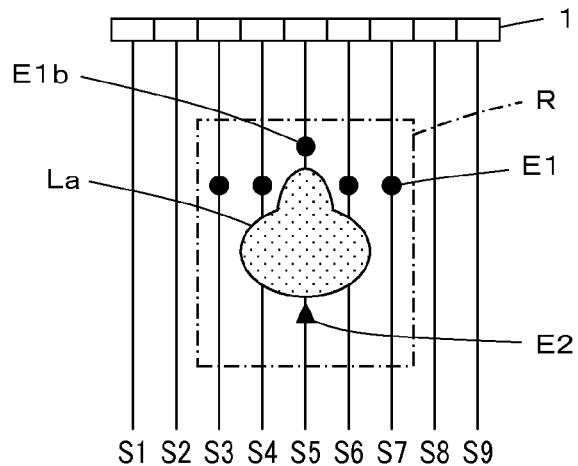
FIG. 12 is a diagram showing set lattice points in a modification of Embodiment 4.

Like the low luminance region La, with regard to a low luminance region which locally protrudes in a shallow direction, for example, as shown in FIG. 12, only lattice points E1b corresponding to protrusions may be set at a shallower position than other lattice points E1. With the use of the lattice points E1 and E1b, similarly, it becomes possible to calculate the local sound speed values of the region between the depth De1 and the depth De2.

Embodiment 5

In Embodiment 4, the number of lattice points which are set at a shallow position from the low luminance region may be adjusted in accordance with the length the depth direction of the low luminance region.

Figure 13A:
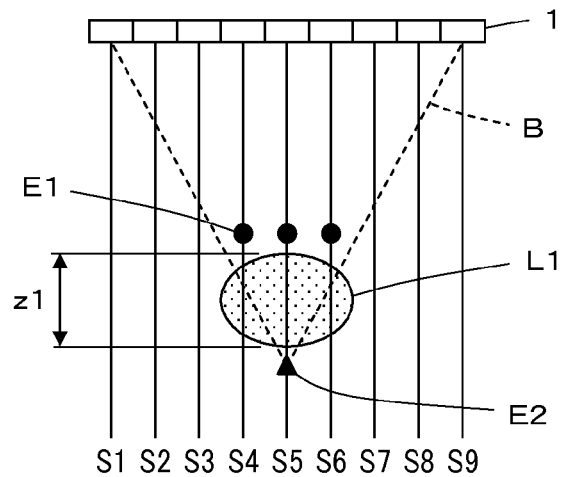
FIG. 13A is a diagram showing the positions of lattice points set when a short low luminance region in a depth direction is provided in Embodiment 5.

For example, as shown in FIG. 13A, it is assumed that three lattice points E1 are set at a shallow position in a low luminance region L1 having a length z1 in the depth direction. At this time, it is preferable that the three lattice points E1 are set in the region of the ultrasonic beam B from the transducer array 1 which forms a transmission focus at a lattice point E2 set at a deep position from the low luminance region L1. This is because a synthesized wave of received waves from a plurality of lattice points E1 at the shallow position having received a received wave from the lattice point E2 at the deep position coincides with a received wave from the lattice point E2 by the Huygens principle, and with the user of this point, the local sound speed values of the low luminance region L1 are calculated.

Figure 13B:
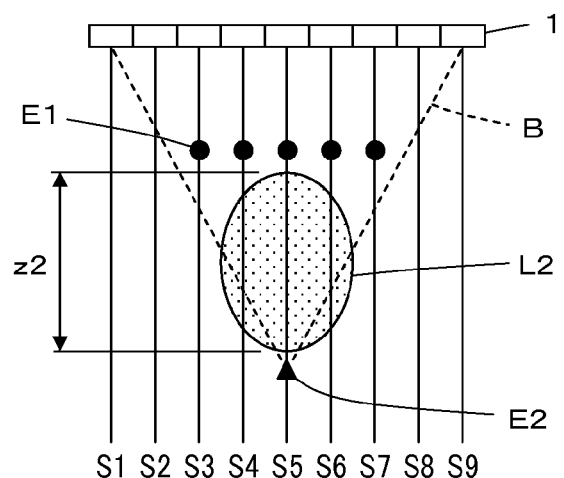
FIG. 13B is a diagram showing the positions of lattice points set when a long low luminance region in a depth direction is provided in Embodiment 5.

For this reason, as shown in FIG. 13B, with regard to a low low luminance region L2 which is located at the same depth as the luminance region L1, is longer than the low luminance region L1, and has a length z2 in the depth direction, five lattice points E1 can be set in the region of the ultrasonic beam B of the transducer array 1 which forms a transmission focus at the lattice point E2 set at the deep position.

In this way, as the length in the depth direction of the low luminance region is long, a large number of lattice points E1 are set at the shallow position, making it possible to more accurately measure the local sound speed values of the low luminance region.

Embodiment 6

In Embodiments 4 and 5, a configuration may be made in which the local sound speed value of the low luminance region is measured and the sound speed map in the region R of interest is produced.

Figure 14:
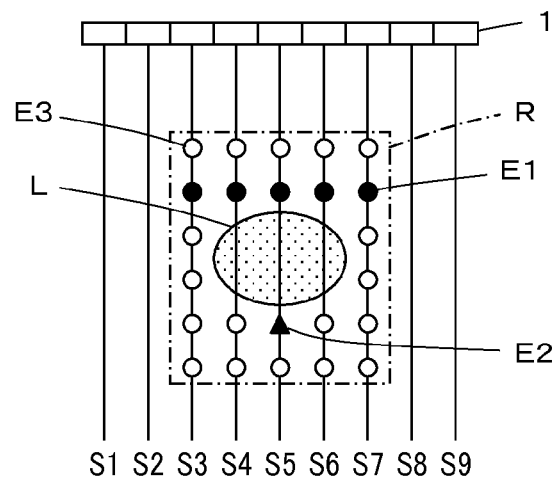
FIG. 14 is a diagram showing set lattice points in Embodiment 6.

For example, as shown in FIG. 14, a region R of interest is set on a B-mode image by an operation from the operating unit 13. If the low luminance region L is detected in the region R of interest by the low luminance region detector 16, the controller 12 sets lattice points E1 and E2 at a shallow position and a deep position from the low luminance region L, and sets a plurality of lattice points E3 for a sound speed map indicated by "○" inside the region R of interest and outside the low luminance region L.

The controller 12 performs control such that the transmission circuit 2 and the reception circuit 3 form a transmission focus at each of the lattice points E1 and E2 and the lattice points E3 for a sound speed map, and transmission and reception of an ultrasonic beam for sound speed measurement are performed, and reception data for sound speed measurement produced by the reception circuit 3 is sequentially stored in the reception data memory 10. As in Embodiments 4 and 5, the sound speed calculator 11 calculates the local sound speed values of the low luminance region L using reception data relating to the lattice points E1 and E2 stored in the reception data memory 10. Meanwhile, the local sound speed values of the lattice points E1, E2, and E3 are calculated using reception data relating to the lattice points E1 and E2 and reception data for a sound speed map relating to the lattice points E3 for a sound speed map, and the sound speed map in the region R of interest is produced in conjunction with the local sound speed values of the low luminance region L.

Data relating to the sound speed map produced by the sound speed calculator 11 is raster-converted by the DSC 5, subjected to various image processes in the image processor 6, and sent to the display controller 7. The B-mode image and the sound speed map are displayed on the monitor 8 in an overlapping manner (for example, display where color or luminance changes depending on the local sound speed value or display where points having the same local sound speed value are connected by a line), or the B-mode image and the sound speed map image are displayed in parallel on the monitor 8 in accordance with the display mode from the operating unit 13 by the operator.

In this way, it becomes possible to measure the local sound speed values of the low luminance region L in the region R of interest and to perform both production of the B-mode image and production of the sound speed map.

Although in Embodiments 4 to 6, reception data output from the reception circuit 3 is temporarily stored in the reception data memory 10, and the sound speed calculator 11 calculates the local sound speed values of the low luminance region in the region R of interest using reception data stored in the reception data memory 10, the sound speed calculator 11 may directly receive reception data output from the reception circuit 3 as input and may calculate the local sound speed values of the low luminance region.

Although in Embodiments 4 to 6, for simplification, the number of openings of the transducer array 1 shown in the drawing, that is, the number of sound rays, the number of lattice points in the region R of interest, and the like are small, the invention is not limited thereto. It is preferable to set the number of openings and the number of lattice points appropriate for diagnosis based on the B-mode image and sound speed measurement.

What is claimed is:

1. An ultrasound diagnostic apparatus comprising:
a transducer array;
a transmission circuit which transmits an ultrasonic beam from the transducer array toward a subject;
a reception circuit which processes reception signals output from the transducer array having received an ultrasonic echo from the subject to produce reception data;
an image producing computing unit which produces a B-mode image on the basis of reception data obtained by the reception circuit;
a region of interest input device which sets a region of interest on the B-mode image produced by the image producing computing unit;
a controller which controls the transmission circuit and the reception circuit so as to perform transmission and reception of ultrasonic beams with forming transmission focuses at a plurality of points set on sound rays at a shallower position and a deeper position than the region of interest set by the region of interest input device to acquire reception data for sound speed measurement; and
a sound speed calculator which calculates an average local sound speed value in the region of interest on the basis of reception data for sound speed measurement,
wherein the points set at the shallower position are set in a shallow point region having a width Wg in an azimuth direction which is determined by a following formula depending on a depth position D1 of the shallowest portion of the region of interest, a width Wr in an azimuth direction and a length H in a depth direction of the region of interest, and a width Wa of simultaneously available transducers for transmission of each ultrasonic beam in the transducer array:

$$Wg = Wr + Wa/[1+(D1/H)].$$

2. The ultrasound diagnostic apparatus according to claim 1,
wherein the range of the points set at the shallower position is set to fall within a region of either ultrasonic beam transmitted with forming a transmission focus at the points set at the deeper position.

3. The ultrasound diagnostic apparatus according to claim 1,
wherein the controller extends the shallow point region as the position of the region of interest set by the region of interest input device gets deeper.

4. The ultrasound diagnostic apparatus according to claim 2,
wherein the controller extends the shallow point region as the position of the region of interest set by the region of interest input device gets deeper.

5. The ultrasound diagnostic apparatus according to claim 1,
wherein the controller extends the shallow point region as the length in the depth direction of the region of interest set by the region of interest input device gets longer.

6. The ultrasound diagnostic apparatus according to claim 2,
wherein the controller extends the shallow point region as the length in the depth direction of the region of interest set by the region of interest input device gets longer.

7. The ultrasound diagnostic apparatus according to claim 1,
wherein the controller extends the shallow point region as the width of simultaneously available transducers for transmission of each ultrasonic beam in the transducer array gets wider.

8. The ultrasound diagnostic apparatus according to claim 2,
wherein the controller extends the shallow point region as the width of simultaneously available transducers for transmission of each ultrasonic beam in the transducer array gets wider.

9. The ultrasound diagnostic apparatus according to claim 1,
wherein the controller further sets additional points at a position between the deeper position and the shallower position, and controls the transmission circuit and the reception circuit so as to perform transmission and reception of ultrasonic beams with forming transmission focuses at all the set points to acquire reception data for a sound speed map, and
the sound speed calculator calculates the local sound speed values of the points on the basis of reception data for a sound speed map and produces a sound speed map in the region of interest.

10. The ultrasound diagnostic apparatus according to claim 2,
wherein the controller further sets additional points at a position between the deeper position and the shallower position, and controls the transmission circuit and the reception circuit so as to perform transmission and reception of ultrasonic beams with forming transmission focuses at all the set points to acquire reception data for a sound speed map, and
the sound speed calculator calculates the local sound speed values of the points on the basis of reception data for a sound speed map and produces a sound speed map in the region of interest.

11. The ultrasound diagnostic apparatus according to claim 3,
wherein the controller further sets additional points at a position between the deeper position and the shallower position, and controls the transmission circuit and the reception circuit so as to perform transmission and reception of ultrasonic beams with forming transmission focuses at all the set points to acquire reception data for a sound speed map, and
the sound speed calculator calculates the local sound speed values of the points on the basis of reception data for a sound speed map and produces a sound speed map in the region of interest.

12. An ultrasound diagnostic apparatus comprising:
a transducer array;
a transmission circuit which transmits an ultrasonic beam from the transducer array toward a subject;
a reception circuit which processes reception signals output from the transducer array having received an ultrasonic echo from the subject to produce reception data;
an image producing computing unit which produces a B-mode image on the basis of reception data obtained by the reception circuit;
a region of interest input device which sets a region of interest on the B-mode image produced by the image producing computing unit;
a low luminance region detector which detects a low luminance region having luminance equal to or lower than a predetermined value in the region of interest set by the region of interest input device;

a controller which sets a plurality of points, on the basis of the low luminance region detected by the low luminance region detector, at a shallower position and a deeper position than the low luminance region and controls the transmission circuit and the reception circuit so as to perform transmission and reception of ultrasonic beams with forming transmission focuses at the set plurality of points to acquire reception data for sound speed measurement; and a sound speed calculator which calculates local sound speed values of the low luminance region on the basis of reception data for sound speed measurement on the assumption that sound speed is uniform between the shallower position and the deeper position, wherein the points set at the shallower position are set in a shallow point region having a width Wg in an azimuth direction which is determined by a following formula depending on a depth position D1 of the shallowest portion of the region of interest, a width Wr in an azimuth direction and a length H in a depth direction of the region of interest, and a width Wa of simultaneously available transducers for transmission of each ultrasonic beam in the transducer array:

$$Wg=Wr+Wa/[1+(D1/H)].$$

13. The ultrasound diagnostic apparatus according to claim 12,
wherein the controller sets a larger number of points at the shallower position than the points set at the deeper position.

14. The ultrasound diagnostic apparatus according to claim 12,
wherein the controller sets a large number of points at the shallower position as the length in the depth direction of the low luminance region detected by the low luminance region detector gets longer.

15. The ultrasound diagnostic apparatus according to claim 13,
wherein the controller sets a large number of points at the shallower position as the length in the depth direction of the low luminance region detected by the low luminance region detector gets longer.

16. The ultrasound diagnostic apparatus according to claim 12,
wherein the controller sets a plurality of points for a sound speed map inside the region of interest and outside the low luminance region, and controls the transmission circuit and the reception circuit so as to perform transmission and reception of ultrasonic beams with forming transmission focuses at the points for a sound speed map to acquire reception data for a sound speed map, and
the sound speed calculator calculates the local sound speed values of the plurality of points for a sound speed map on the basis of reception data for a sound speed map, and produces a sound speed map in the region of interest in conjunction with the local sound speed values of the low luminance region.

17. The ultrasound diagnostic apparatus according to claim 13,
wherein the controller sets a plurality of points for a sound speed map inside the region of interest and outside the low luminance region, and controls the transmission circuit and the reception circuit so as to perform transmission and reception of ultrasonic beams with forming transmission focuses at the points for a sound speed map to acquire reception data for a sound speed map, and the sound speed calculator calculates the local sound speed values of the plurality of points for a sound speed map on the basis of reception data for a sound speed map, and produces a sound speed map in the region of interest in conjunction with the local sound speed values of the low luminance region.

18. The ultrasound diagnostic apparatus according to claim 14,
wherein the controller sets a plurality of points for a sound speed map inside the region of interest and outside the low luminance region, and controls the transmission circuit and the reception circuit so as to perform transmission and reception of ultrasonic beams with forming transmission focuses at the points for a sound speed map to acquire reception data for a sound speed map, and
the sound speed calculator calculates the local sound speed values of the plurality of points for a sound speed map on the basis of reception data for a sound speed map, and produces a sound speed map in the region of interest in conjunction with the local sound speed values of the low luminance region.

19. A method of producing an ultrasound image, the method comprising the steps of:
transmitting an ultrasonic beam from a transducer array toward a subject on the basis of driving signals supplied from a transmission circuit;
processing reception signals output from the transducer array having received an ultrasonic echo from the subject by a reception circuit to produce reception data;
producing a B-mode image on the basis of obtained reception data;
setting a region of interest on the produced B-mode image;
setting a plurality of points on sound rays at a shallower position and a deeper position than the set region of interest, the points set at the shallower position being set in a shallow point region having a width Wg in an azimuth direction which is determined by a formula $Wg=Wr+Wa/[1+(D1/H)]$ depending on a depth position D1 of the shallowest portion of the region of interest, a width Wr in an azimuth direction and a length H in a depth direction of the region of interest, and a width Wa of the simultaneously available transducers for transmission of each ultrasonic beam in the transducer array;
performing transmission and reception of ultrasonic beams with forming transmission focuses at the set points to acquire reception data for sound speed measurement; and
calculating an average local sound speed value of the region of interest on the basis of acquired reception data for sound speed measurement.

20. A method of producing an ultrasound image, the method comprising the steps of:
transmitting an ultrasonic beam from a transducer array toward a subject on the basis of driving signals supplied from a transmission circuit;
processing reception signals output from the transducer array having received an ultrasonic echo from the subject by a reception circuit to produce reception data;
producing a B-mode image on the basis of obtained reception data;
setting a region of interest on the produced B-mode image;
detecting a low luminance region having luminance equal to or lower than a predetermined value in the region of interest;
setting a plurality of points at a shallower position and a deeper position than the detected low luminance region on the basis of the detected low luminance region, the points set at the shallower position being set in a shallow point region having a width Wg in an azimuth direction which is determined by a formula $Wg=Wr+Wa/[1+(D1/H)]$ depending on a depth position $D1$ of the shallowest portion of the region of interest, a width Wr in an azimuth direction and a length H in a depth direction of the region of interest, and a width Wa of the simultaneously available transducers for transmission of each ultrasonic beam in the transducer array;

performing transmission and reception of ultrasonic beams with forming transmission focuses at the set points to acquire reception data for sound speed measurement; and calculating local sound speed values of the low luminance region on the basis of acquired reception data for sound speed measurement on the assumption that sound speed is uniform between the shallower position and the deeper position.

* * * * *